United States Patent [19]

Hsu et al.

[11] Patent Number: 5,408,322
[45] Date of Patent: Apr. 18, 1995

[54] SELF ALIGNING IN-SITU ELLIPSOMETER AND METHOD OF USING FOR PROCESS MONITORING

[75] Inventors: Jon S. Hsu; Bhola N. De, both of Congers; Rodney L. Robison, Kingston; Tugrul Yasar, Woodstock, all of N.Y.

[73] Assignee: Materials Research Corporation, Orangeburg, N.Y.

[21] Appl. No.: 52,888

[22] Filed: Apr. 26, 1993

[51] Int. Cl.⁶ ............................ G01J 4/00; G02F 1/01
[52] U.S. Cl. ................................. 356/369; 356/382; 250/225
[58] Field of Search ............... 356/364–369, 356/381, 382, 351, 355, 357, 243, 399, 400, 401; 250/560, 561, 225

[56] References Cited

U.S. PATENT DOCUMENTS

| 3,880,524 | 4/1975 | Dill et al. | 356/369 |
| 4,077,720 | 3/1978 | Kasai | 356/369 |
| 4,983,823 | 1/1991 | Isobe | 356/382 |

FOREIGN PATENT DOCUMENTS

| 0352004 | 1/1990 | European Pat. Off. | |
| 0041331 | 3/1983 | Japan | 356/369 |
| 9212404 | 7/1992 | WIPO | |

OTHER PUBLICATIONS

Applied Optics, vol. 14, No. 1, Jan. 1975, article entitled "High Precision Scanning Ellipsometer" by D. E. Aspnes and A. A. Studna.
Ellipsometry and Polarized Light–Azzam & Bashara, North-Holland, 1987 pp. 282–289; pp. 232–341.

*Primary Examiner*—Hoa Q. Pham
*Attorney, Agent, or Firm*—Wood, Herron & Evans

[57] ABSTRACT

An ellipsometric measuring system is set-up in association with a vacuum chamber on a production line for thin film samples. The ellipsometer has a scanner for directing the incident light beam to different locations on a thin film sample, and the ellipsometer also has an aperture for limiting the reflected light beam received by the photodetector. The scanner implements a method of aligning the incident beam to a selected surface of the sample. The scanner and the aperture are used to provide a finer adjustment of the incident beam with respect to the selected surface. The ellipsometric measuring system further uses test thin film samples with known film thicknesses and index or refractions to calculate a value for the angle of incidence of the incident light beam.

21 Claims, 4 Drawing Sheets

SELF ALIGNING IN-SITU ELLIPSOMETER AND METHOD OF USING FOR PROCESS MONITORING

BACKGROUND OF THE INVENTION

1. Field of the Invention

The present invention relates to the in-process measurement of thin film sample characteristics, and more particularly to self-aligning in-situ ellipsometers used on-line to automatically measure the characteristics of the thin film samples.

2. Description of the Related Art

The manufacture of semiconductor products typically requires the deposition of successive thin film layers on a substrate, which hereinafter will be referred to as a thin film sample. The deposition of thin film layers occurs by passing the substrate through successive vacuum chambers on a production line. At different stages of the manufacturing process, it is often necessary to precisely measure various characteristics of those thin film layers, for example, index of refraction and film thickness. Often those characteristics need to be determined at close to monolayer, that is single atomic or molecular layer, accuracy. To perform those measurements the thin film samples are removed from the production line and taken to a measurement station in a laboratory at which an ellipsometer has been precisely set up and calibrated. The ellipsometer provides data relating to changes in the polarization of light reflected from surfaces of the thin film sample.

The apparatus and methods of using a rotating analyzer in a laboratory to measure the thickness and index of refraction of a thin film on a substrate is well known, see for example, "High Precision Scanning Ellipsometer" by D. E. Aspnes and A. A. Studna and published in Applied Optics, Vol. 14, No. 1, January, 1975. The article describes the determination of the complex reflectance ratios, film thickness, index of refraction and the ellipsometric parameters. In the laboratory, a goniometer, an instrument for precisely measuring angles, is used to determine the angle of incidence of the light beam onto the sample. Using a thin film sample for which the ellipsometric parameters $\Psi$ and $\Delta$ are known, the article describes the collection of light intensity data as a function of the analyzer angle over many analyzer revolutions. The collected data is used to calculate Fourier transform coefficients which in turn are used to calculate the calibration parameters which include an analyzer parameter As, a polarizer parameter Ps, and an attenuation parameter $\eta$. Next, using a thin film sample for which the film thickness and index of refraction are unknown, the above process of collecting data and calculating the Fourier transform coefficients is repeated. The complex reflectance ratio $\rho$ is calculated afterwhich experimental ellipsometric parameters $\Psi$ and $\Delta$ are determined and stored. For purposes of this disclosure, the ellipsometric parameters will always refer to the variables $\Psi$ and $\Delta$.

Next calculated values of the ellipsometric parameters are determined using a models described in the book *Ellipsometry and Polarized Light*, by Azzam and Bashana, published by North-Holland, 1987. Pages 332–340, "Reflection and Transmission by Isotropic Stratified Planar Structures" describe analysis of reflected light in a multi-film structure. The model is constructed of a series of scattering matrices. For a single layer thin film sample of $SiO_2$ on a Si substrate, the model is comprised of a first interface matrix $I_{01}$ between ambient air and the $SiO_2$ layer; a layer matrix $L_1$ comprised of $SiO_2$; and a second interface matrix $I_{12}$ between the $SiO_2$ layer and the substrate of Si. The interfaces are modeled pursuant to the discussion at pages 283–287 of the book, subtitled "Reflection and Transmission by an Ambient-film-substrate System". In the above model, an expression for film phase thickness $\beta$ utilizes variables representing film thickness d, the film complex index of refraction N, and the angle of incidence $\Phi$. In the laboratory setup, the angle of incidence is known and the film thickness is assumed to be equal to the desired value from the manufacturing process. The values of N for air and silicon are well known and used. The real component of the value of N, the index of refraction, for the thin film, for example, $SiO_2$, is estimated to be its expected value. The imaginary component of the value of N for the thin film layer is assumed to be zero. From the above assumptions, the film phase thickness is determined, and thereafter, the overall complex reflection coefficients and ratios are calculated from which calculated values of the ellipsometric parameters may be determined. An error function, such as a root mean square difference function, is used to compare the experimental and calculated values of the ellipsometric parameters. The above process is repeated for new values of the film thickness and index of refraction of the thin film layer until a minimum for the error function is found. The estimated values of film thickness and index of refraction producing the minimum error function are considered to be the final solution values. It is well known to implement the above models with a computer analysis.

The above well known post process off-line measurement of the characteristics of production samples has the disadvantage of requiring additional manual handling of the production samples. The increased handling adds substantial time to the total processing time and exposes the samples to undesirable contamination.

The off-line process has a further difficulty in aligning the reflection of the light beam from the sample onto the photodetector which measures the intensity of the reflected light beam. Various procedures exist which involve adjusting the light beam or manipulating the sample. Both of those techniques have disadvantages. For example, each time the light beam is adjusted, the angle of incidence is changed and must be measured again. Adjusting the orientation of the sample requires a fixture with mechanisms for changing the orientation of the thin film sample with great precision. Such a fixture is expensive to make and time consuming to use.

Measuring the characteristics of thin film samples while they are on a production line reduces exposure of the samples to contamination and reduces total processing time. However, the samples on the production line are in a vacuum chamber and not readily accessible. Further, automatic handling of the samples on a production line may result in one or more samples having a slightly different orientation which will change the position of the reflected light beam from the sample with respect to the photodetector of the ellipsometer.

SUMMARY OF THE INVENTION

To overcome the disadvantages of having to measure thin film layers at a point remote from the production line, the present invention provides a rotating analyzer ellipsometer in-situ on a production line which will automatically measure film layer characteristics of the thin film samples.

A vacuum chamber, which is dedicated to the measuring process, is located at a selected position in a production line. An ellipsometer is mounted proximate the vacuum chamber which has two opposed sidewall windows. A light source and photodetector are also respectively mounted on opposite sides of the vacuum chamber. An X-Y scanner receives light from the light source and aims an incident light beam through one of the windows and onto the thin film sample located in the chamber. A reflected light beam passes through the opposite window and a pin hole aperture is used to limit the quantity of the reflected light beam which is received by the photodetector. The invention further provides a method of aligning the incident light beam to a predetermined surface of the thin film sample, and further moving the incident light beam with the scanner to a position providing maximum light intensity of the reflected light beam through the aperture and onto the photodetector.

Using test samples having a known film thickness and index of refraction, the previously described model and error function are used with assumed values of the angle of incidence to calculate and store a precise angle of incidence. A number of test samples are used to calculate a respective number of angles of incidence and an average angle of incidence is then calculated and stored for use in subsequent calculations. A production thin film sample is subsequently moved proximate the ellipsometer; and using the X-Y scanner, the incident light beam is moved to a position producing a reflected light beam from the desired surface of the production sample. The ellipsometer is then used with the stored angle of incidence in a manner identical to that described with regard to the off-line measurements to determine the film thickness and index of refraction of the production thin film sample.

By virtue of the foregoing, there is provided a self-aligning in-situ ellipsometer for measuring thin film layer characteristics of thin film samples on the production line thereby having the advantages of minimizing handling of the thin film samples, reducing the potential for contamination and reducing the overall cycle time. The X-Y scanner and pin hole aperture facilitate automatic calibration of the ellipsometer which may be performed at any time.

These and other objects and advantages of the invention shall be made apparent from the accompanying drawings and the description thereof.

BRIEF DESCRIPTION OF THE DRAWINGS

The accompanying drawings, which are incorporated in and which constitute part of the specification, illustrate embodiments of the invention and, together with the description given above, and the detailed description given below, serve to explain the principles of the invention.

FIG. I is a schematic block diagram illustrating the use of an X-Y scanner and pin hole plate with a rotating analyzer ellipsometer in association with a vacuum chamber on a production line.

DETAILED DESCRIPTION OF THE INVENTION

Figure 1:
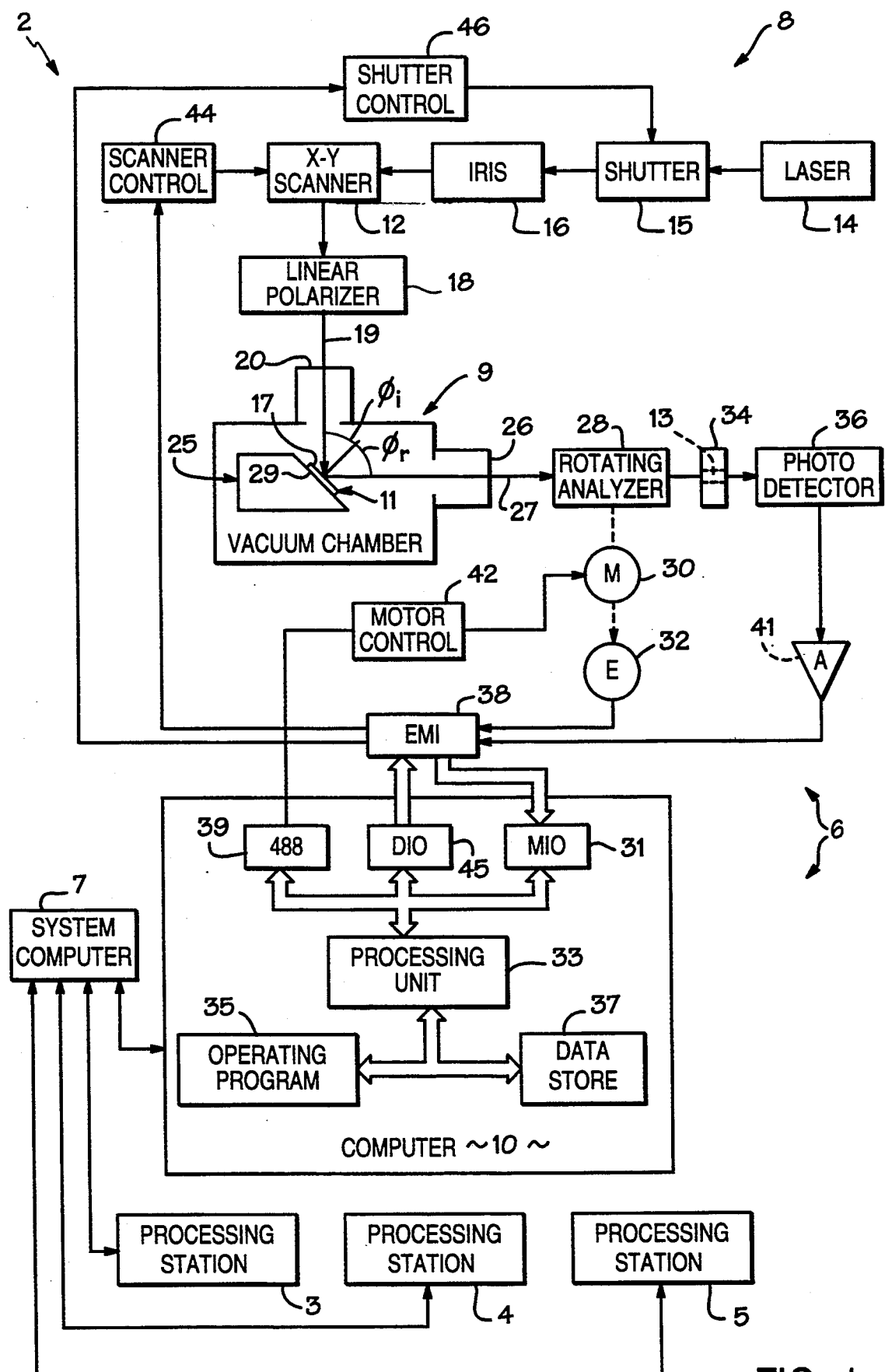

FIG. 1 illustrates a production line 2 in which a series of processing stations includes those schematically illustrated as processing stations 3, 4 and 5. Each of the processing stations are effective to perform one or more steps of the process required to produce a thin film sample comprising one or more thin film layers on a substrate. The processing stations may provide sputtering, chemical vapor deposition or other methods of manufacturing thin films. The samples are moved from one processing station to another by well known transfer mechanisms and the processing stations of the production line 2 are under control of a system computer 7. At one or more points in the process, it may be desirable to measure the characteristics of the thin film layers, such as film thickness and index of refraction. To execute those measurements on-line, that is in-situ on the production line, a processing station dedicated to that measurement process is added to the production line as illustrated by processing station 6 of the FIG. 1. The measurement processing station 6 is comprised of an ellipsometer 8 mounted proximate a vacuum chamber 9 and under control of measuring station computer 10. When it is determined that thin film measurements should be made, the system computer 7 is operative to cause a thin film sample to be transferred from another station on the production line to the measuring station 6 and positioned within the vacuum chamber 9. As the thin film sample 11 is transferred into the vacuum chamber 9, it will be placed at a predetermined position. However, because of uncontrollable variations in the process, each sample will most probably have a slightly different orientation, that is, the sample may be very slightly tilted one way or another after it is in its predetermined position. The slightest changes in orientation of the sample will adversely impact the accuracy of the measurements made by the ellipsometer 8. Therefore, an X-Y scanner 12 is used with the ellipsometer 8. Under the control of the measuring station computer 10, the X-Y scanner 12 aligns the incident light beam of the ellipsometer 8 onto the sample 11 to its precise position. In addition, a pin hole 13 is used to limit the reflective light from the sample thereby optimizing the measurements made by the ellipsometer.

Thereafter, the measuring station computer 10 controls the operation of the ellipsometer 8 to collect the data relating to the thin film layer characteristics on the thin film sample 11. Thereafter, in accordance with the well known methods and techniques, the measuring station computer 10 calculates ellipsometric parameters and utilizes a computer model to calculate values for the film thickness and index of refraction of the thin film layer on the sample 11.

Referring to the structure of FIG. 1 in more detail, a collimated light source 14 produces a light beam which passes through a shutter 15 be produced by various devices, such as an iris 16 and into X-Y scanner 12. A collimated light beam can be, for example, a He—Ne laser, or other laser sources, a gas discharge type arc lamp source with collimating optics assembly, a light emitting diode with collimating optics assembly, or a laser diode. A beam splitter, fiber optics or other devices may be used to transport or transform the light beam before it is incident on scanner 12. The laser light output from X-Y scanner 12 is linearly polarized light 19 by polarizer 18. The linearly polarized beam 19 passes through a quartz window 20 mounted in the wall on one side of vacuum chamber 9. The incident light beam 19 strikes the sample 11 located on a movable pallet 25 at an angle of incidence $\Phi_i$. A reflected light beam 27 is reflected off the surface of the sample at an angle of reflection, $\Phi_r$ equal to the angle of incidence $\Phi_i$. The reflected light beam 27 passes through a second quartz window 26 mounted in the wall of another side of the vacuum chamber 9.

The reflected light beam 27 then passes through an analyzer 28 mechanically coupled to a motor 30 which rotates the analyzer 28 about an axis generally defined by the optical path of the reflected light beam 27. An encoder 32 is mechanically coupled to the motor 30 and measures the changes in the angular position of the analyzer 28. After passing through the analyzer 28, the re-reflected light beam 27 passes through an aperture 13 in a pin hole plate 34 and is received by a silicon photodetector 36. The silicon photodetector 36 produces an output signal voltage proportional to the intensity of the light it receives. Other photodetectors, photosensors or photodiodes may be used depending on the wavelength of the light and polarization sensitivity.

An electromagnetic interference (EMI) protection interface circuit 38 receives the output pulses from the encoder 32 and an output signal from an amplifier 41 which amplifies the output signal voltage produced by the photodetector 36. The signals are input to the computer 10 via a MIO input interface 31 which is a data acquisition board model no. AT-MIO-112L-5 commercially available from National Instruments located in Austin, Tex. The computer 10 is a personal computer having 386 processing unit 33 commercially available from Intel and running at 33 MHz. The operating programs 35 include a DOS based operating system which is effective to control the operation of processing unit 33. Data signals such as those obtained from amplifier 41 and values calculated by processor 33 are stored in data store 37. The processing unit 33 produces control signals to motor controller 42 via an IEEE-488 interface board 39 commercially available from Metrabyte located in Taunton, Mass. The processing unit 33 produces output signals to the interface circuit 38 via a DIO output interface board 45 which is a digital I/O board model no. AT-DIO-32F commercially available from National Instruments located in Austin, Tex.

The interface circuit 38 is an electronic control box using electromagnetically shielded wire and is located near the computer 10. When the computer 10 is ready for data acquisition, the circuit 38 enables an internal acquisition hold-off circuit. When the motor 30 reaches a home position of the encoder 32, encoder pulses are passed to the external conversion pin of MIO 31. For each encoder pulse reaching the conversion pin, the analog signal voltage from amplifier 41 is measured, converted to a digital signal and stored in data store 37. In addition, control signals are produced by a control circuit comprised of the computer 10, the interface 38 and a scanner control 44 to operate the scanner 12. The computer produces further control signals through the interface 38 to a shutter control 46, controlling the shutter 15. With the exception of the X-Y scanner 12, scanner control 44, quartz windows 20 and 26, vacuum chamber 9 and pin hole plate 34, all of the other components of FIG. 1 are utilized in the off-line measurement of physical characteristics of thin film samples. Further, except as noted herein, there is no difference in their function and operation whether used for off-line measurements or on-line measurements.

The X-Y scanner 12 located with respect to the incident light beam is used to direct the incident light beam 19 to different locations across the surface of the thin film sample in a predetermined raster scan pattern. Scanning the surface of the thin film sample changes the optical path of the incident light beam striking the sample and, therefore, moves the reflected light beam with respect to the aperture and the photodetector. When the incident light beam 19 strikes the thin film sample, light is reflected from the optically flat front surface 17 as well as from the rear surface 29. The contribution of reflected light from the rear surface 29 depends on the transparency of the sample and the texture of the rear surface 29. If the sample is transparent and has a rear surface 29 which is relatively rough, light will be reflected from the rear surface 29 in a diffuse manner. In contrast, if the rear surface 29 is flat, light will be reflected similarly from both the rear and the front surfaces; but the reflected light beams will be displaced from each other. The computer 10 generates scanning control signals to the scanner control 44 which commands the scanner 12 to move the incident light beam 19 in such a way as to direct the reflected light beam 27 from a selected surface of the sample through the pin hole plate 34 and onto the detector 36.

The computer 10 provides control signals to the scanner control 44, which in turn controls the X-Y scanner in the execution of a predetermined scanning pattern. The predetermined scanning pattern is initiated at a location such that the reflected light beam 27 from the selected surface strikes the aperture 13 and photodetector 36 prior to the reflected light beam 27 from the rear surface 29. For example, referring to FIG. 1, if the selected surface is the front surface 17, the scanner would begin scanning from the bottom of the sample as viewed in FIG. 1, that is, at a point closer to the analyzer. If the rear surface 29 is the selected surface, the scanning pattern would begin at the top, that is, at a point closer to the scanner. For purposes of this disclosure, the Y axis refers to an axis crossing the surface of the sample and defined by a projection of the light beam path onto the front surface 17 of the sample. The X axis crosses the surface of the sample perpendicular to the Y axis. The origin, or intersection of the X and Y axes relative to the front surface of the sample is a matter of design choice.

Figure 2:
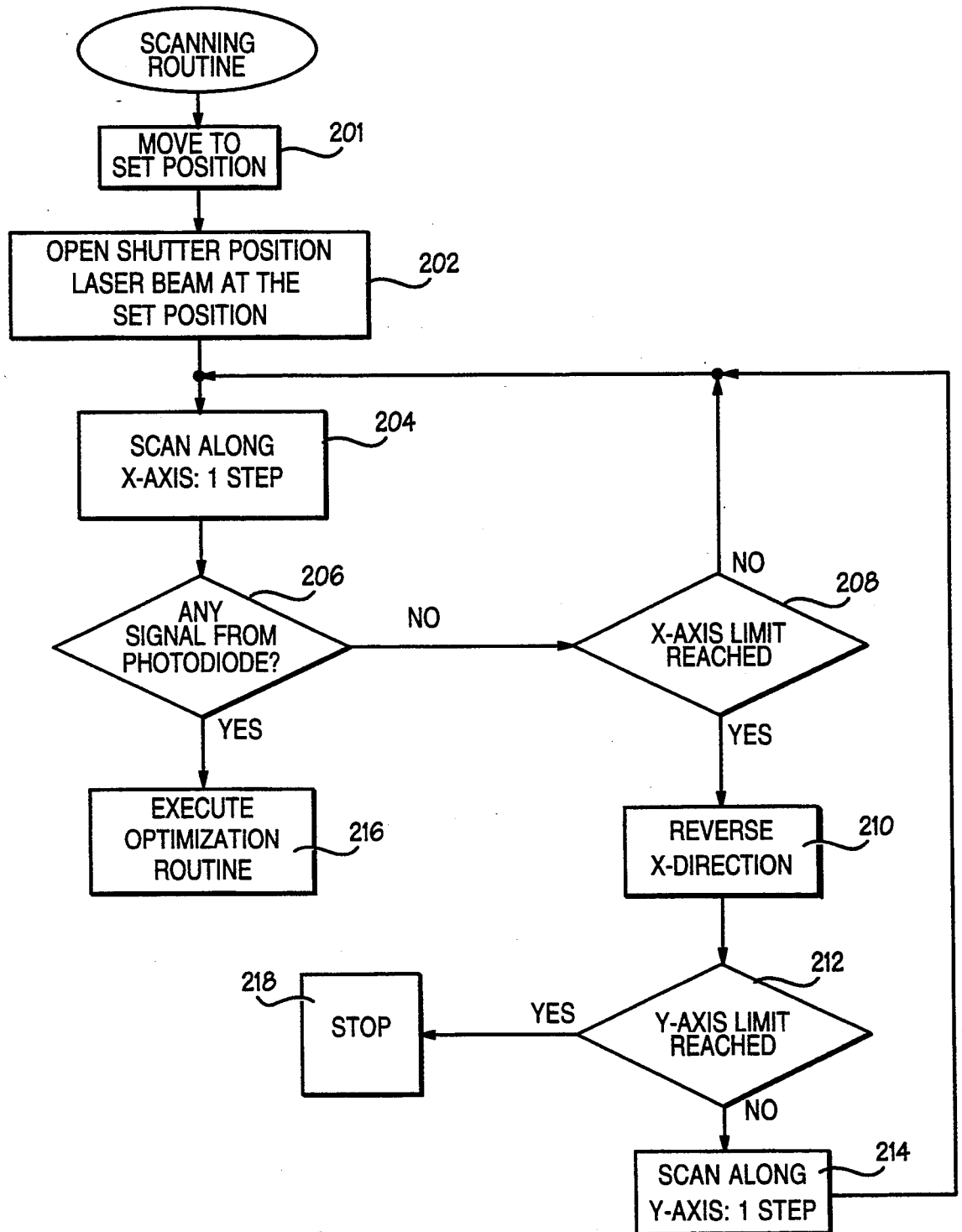
FIG. 2 is a flowchart of a routine for operating the X-Y scanner to locate a reflected beam from a desired surface of the sample.

The routine executed by the computer 10 to control the X-Y scanner pursuant to a self-aligning beam capture algorithm is illustrated in FIG. 2. At step 201, the computer first commands the scanner control 44 to move the scanner 12 to a set position. If the scanning routine has been previously executed to locate the selected surface, such as in scanning a test sample during a calibration routine, the scanner position providing the optimum reflection from the selected surface was stored and may be used as the set position. Therefore, the coordinates of that position are read from the data stored within the computer 10 and used to position the scanner at the set position or starting position. Alternatively, if no prior set position has been defined, the scanner may be moved to a default set position such that moving the incident light beam in the predetermined pattern will result in the reflected light beam from the selected surface being detected by the photodetector prior to a reflected beam from another surface. That set position may be determined from the size of the laser beam and its approximate area of intersection with the sample. Pursuant to process step 202, the computer then commands the shutter control 46 to open the shutter 15, thereby providing the light beam to the X-Y scanner 12.

Next, at process step 204, the computer commands the scanner control 44 to control the X-Y scanner 12 to move the incident light beam 19 a predetermined incremental step along the X axis. A step is a predetermined incremental displacement in the desired direction. The initial direction of motion along the X axis is a matter of design choice. At process step 206, the computer monitors the output from the photodetector 36 and amplifier 41 to determine if an output signal is present. If not, at process step 208, a check is made to determine whether the X axis limit has been reached. The limit may be a determined as a function of the size of the beam and the anticipated area of intersection of the beam on the sample. If the X axis limit has not been reached, process steps 204 and 206 are iterated until the X axis limit is reached. At that point, the direction of motion in the X axis is reversed, per process step 210, and at process step 212 a check is made to determine whether the Y axis limit has been reached. If not, process step 214 requires that the scanner move the incident light beam 19 along the Y axis by a predetermined incremental step; and the above process is repeated causing the laser beam to move a in a raster scan pattern across the surface of the sample.

The raster scan continues until, at process step 206, the computer detects an output signal from the photodetector 36. Thereafter, per process step 216, a beam optimization routine, discussed in greater detail below, is executed to find the exact position which provides the optimum intensity of the reflected light beam 27 from the selected surface. If both the X and Y limits are reached without any output signal being detected from the photodetector 36, the process at step 218 stops and provides an error message to the system computer. The scanner is Model No. XY0507S; the scanner control is Model No. DX2005; and both are available from General Scanning located in Watertown, Mass.

Figure 3:
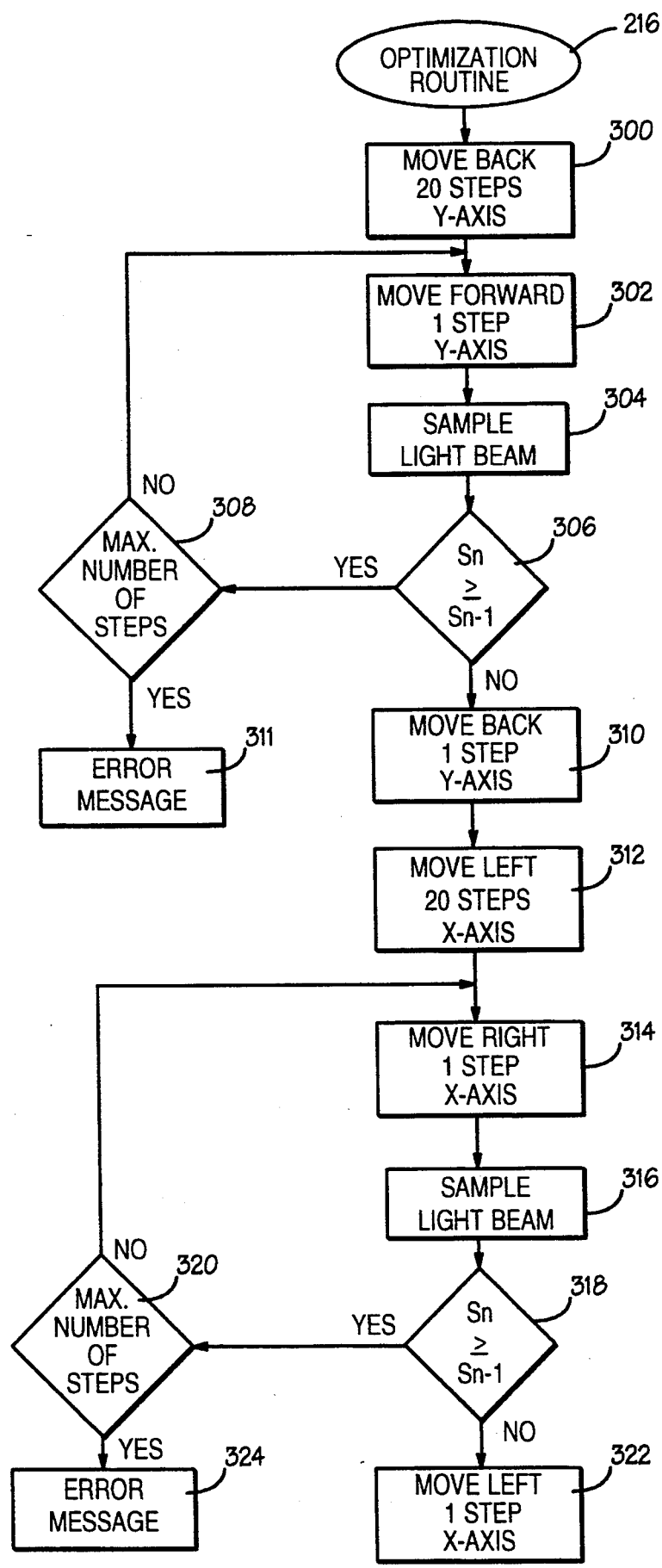
FIG. 3 is a flowchart of a routine for using the X-Y scanner and the reflected beam through the pin hole to find the scanner position producing optimum signal strength.

FIG. 3 illustrates a flowchart of an optimization routine executed by the computer 10 to use the X-Y scanner with the reflected light received by the photodetector 36 through the pin hole plate 34. The scanning routine described with respect to FIG. 2, is effective to locate the reflected light beam 27 from the predetermined or front surface 17 of the sample through the pin hole plate 34 and onto the detector 36. The function of the routine of FIG. 3 is to further refine the position of the reflected light beam 27 with regard to the pin hole plate 34. A further scanning pattern is executed to direct the incident light beam to different locations on the thin film sample. The intensity of the reflected light beam is measured by the photodetector at each location, and the incident light beam is moved to a location providing the maximum intensity of the reflected light beam through the pin hole plate 34 and onto the detector 36. Moving the incident beam to a position providing maximum signal strength of the reflected beam will improve the subsequent sampling process used to determine the analyzer angle and ellipsometric parameters.

At step 300, the process first requires that the reflected beam be moved back along the Y axis a predetermined distance, for example, twenty steps. Referring to FIG. 1, the reflected beam would be moved over the surface of the sample toward the analyzer 28. This motion of twenty steps may result in the reflected beam moving off the aperture on the pin hole plate 34. Next, at step 302, the X-Y scanner is commanded to move the incident beam 19 thereby moving the reflected beam one step in the reverse direction along the Y axis, that is, away from the analyzer 28. Next, at step 304, the computer 10 samples the reflected light beam by detecting and storing a current magnitude of the output signal from the amplifier 41. The computer then, per process step 306, compares the current magnitude of the current sample $Sy_n$ with a prior magnitude of the previous sample $Sy_{n-1}$. If the current magnitude of the current sample is greater than or equal to the prior magnitude of the previous sample, at step 308, the process first checks to determine whether the maximum number of steps have been taken; and if not, the process returns to step 302. The steps of moving forward one increment, sampling the output signal from the detector 36 and comparing the magnitude of the current sample to the prior sample, is iterated until the current sample is found to be less than the previous sample. When that determination is made, motion of the incident light beam in the current direction is stopped; and the process, at step 310, instructs the X-Y scanner 12 to move the incident beam 19 one step back along the Y axis toward the analyzer. Consequently, the incident light beam 19 will be positioned at a point which it has the greatest light intensity through the pin hole 13 and onto the detector 36.

If the above process is iterated to move the reflected light beam 27 a maximum number of steps as determined by process step 308, and a maximum signal strength has not been detected, it is arbitrarily decided that the process will not find a maximum signal strength in implementing the current algorithm. Therefore, the process is terminated; and at step 311, an error message is displayed to the operator. The maximum number of steps detected in process step 308 is typically twice the number of steps the beam was moved at process step 300.

Process steps 300–310 are effective to locate the maximum beam intensity along the Y axis. The strategy of that process is repeated in process steps 312–322 to move the incident light beam 19 along the X axis in order to locate the position of maximum signal strength. At step 312, the computer commands the X-Y scanner to move the incident light beam 19 twenty steps in the left direction along the X axis. The direction of motion, right or left along the X axis at step 312, is arbitrary and a matter of design choice. At step 314, the computer commands the X-Y scanner to move the incident light beam 19 one step to the right along the X axis. At step 316, the output of amplifier 41 is sampled; and at step 318, the current magnitude of that output signal $Sx_n$ is compared to the magnitude of the previous sample $Sx_{n-1}$. As long as the current sample is greater than or equal to the previous sample, the process iterates through steps 314–320. When the magnitude of the current sample is found not to be greater than or equal to the magnitude of the previous sample, at step 322 the computer instructs the X-Y scanner stop motion of the incident light beam in the current direction and to move the incident beam 19 one step to the left along the X axis. The process at step 320 will terminate if the algorithm is not satisfied within a predetermined maximum number of steps, typically taken to be twice the number of steps moved in process step 312. In that event, an error message is presented to the operator per step 324.

When the optimization routine is complete, the reflected beam 27 is located with respect to the aperture such that the maximum possible signal strength is being measured by the detector 36. The choice of whether to move in the X-axis first or the Y-axis first is arbitrary. The optimization routine uses pin hole plate 34 Model No. 04PPM017, commercially available from Melles Griot located in Irvine, Calif. The use of the pin hole plate 34 improves the discrimination in the detection of maximum signal strength and improves the accuracy of calculations of various parameters. The diameter of the pin hole is 0.2 mm. However, an iris 16 with an adjustable pin hole, or other pinholes with different diameters may also be used. The quartz windows 20 and 26 must be chosen so that the light beam is not scattered and the polarization is not changed. The quartz windows 20 and 26 must also have low stress induced birefringence effects and are commercially available from the Bomco Corporation located in Gloucester, Mass.

The use of the apparatus of FIG. 1 to facilitate the measurement of film thickness and index of refraction of thin film layers on thin film samples will be described below. For this discussion, the measurements will require detecting a reflected beam 27 from the front surface 17 of the sample. The operation of the ellipsometer in conjunction with the vacuum chamber 9 is controlled by a computer 10 which is electrical communication with a system computer 7. The system computer 7 typically has overall control of the process and the transfer of samples between the vacuum chambers. The operation and integration of a system computer 7 with a local vacuum chamber controller, such as computer 10, is well known.

Prior to the ellipsometer being used in production, the measuring system must be calibrated. Further, it may be desired to recalibrate the system at arbitrary intervals based on time or production volume. The calibration may be done automatically or manually. The calibration process requires that a calibration sample which may be $SiO_2$ on silicon or gold or other thin film sample having known calibration parameters, that is, a polarizer parameter Ps, an analyzer parameter As, and an attenuation parameter eta, $\eta$. The calibration sample is manually or automatically loaded in the vacuum chamber. The scanning process and optimization routine, as previously described, is executed to locate the front surface of the calibration sample after which a calibration process is initiated.

The remainder of the on-line calibration process is identical to that previously described with regard to calibrating an off-line ellipsometer. For a given polarizer angle, the computer 10 provides control signals to the motor controller 42 to command the motor 30 to rotate the crystal of the analyzer 28 a predetermined number of revolutions, for example, 100. During each revolution of the analyzer, the light intensity incident on the photodetector changes; and the encoder generates a predetermined number of output pulses, for example, 250. For each encoder pulse detected by the computer 10, the computer samples the signal strength of the reflected light beam 27 by sampling the output signal voltage of the amplifier 41. If the encoder generates 250 pulses per revolution, then in 100 revolutions of the analyzer, 2500 data points representing samples of the output signals would be collected and stored in association with the respective encoder positions. An FAT analysis is performed on the data points to calculate the of two Fourier coefficients. The polarizer angle is then changed by a predetermined angle, and the above process is repeated. A series of measurements is performed for polarizer angles that change by successive increments in order to calculate the Fourier coefficients. The polarizer may be set to the different angles either manually or by a motor drive under the control of the computer 10. Using the calculated Fourier coefficients, the system is then calibrated to the known calibration parameters, Ps, As, and $\eta$ of the calibration sample.

Figure 4:
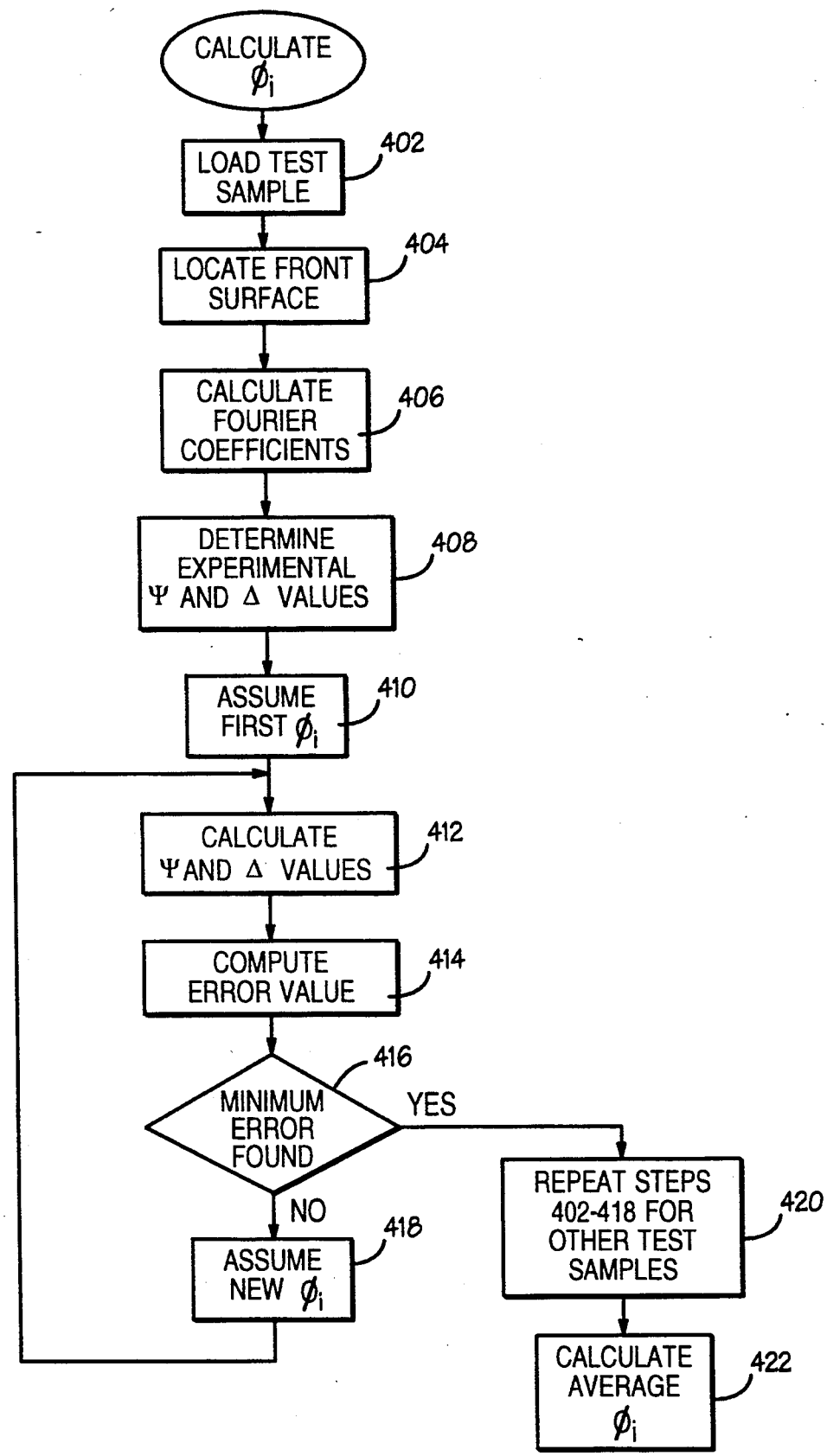
FIG. 4 is a flowchart of the process for using the ellipsometer to determine an angle of incidence.

After the system has been calibrated, the angle of incidence must be precisely determined. Although an angle of incidence is predetermined by the ellipsometer set-up with respect to the vacuum chamber, changes in orientation of the pallet holding the wafers dictate a refinement of that designed angle of incidence. FIG. 4 is a flow chart illustrating the process for calculating the angle of incidence. The first step 402 requires that a first test sample for which the film thickness and index of refraction are known be loaded into the measurement chamber. The scanning and optimization routines are executed to detect the front surface of the sample as required by step 404. In a manner identical to that described in the Aspnes and Studna article referenced earlier, the ellipsometer is used to collect data; and the Fourier coefficients are calculated per step 406. At step 408, the Fourier coefficients and the calibration parameters are used to calculate experimental values of the ellipsometric parameters $\Psi$ and $\Delta$; and those experimental values of the ellipsometric parameters are stored.

Next, using the same models described in the Azzam and Bashana book previously referenced, the angle of incidence is precisely determined. As previously discussed, the model uses an expression for film phase thickness $\beta$ which has variables representing film thickness d, the film complex index of refraction N, and the angle of incidence $\Phi$. In the off-line laboratory setup described earlier, the angle of incidence is known and estimates are made for the film thickness and index of refraction. In precisely calculating the angle of incidence for the on-line in-situ ellipsometer, the film thickness and angle of incidence of the sample are known and used; and a value for the angle of incidence is assumed. Therefore, at step 410, a first angle of incidence is assumed; and at step 412, using the known values of index of refraction and film thickness of the test sample, calculated values of the ellipsometric parameters $\Psi$ and $\Delta$ are determined.

If, for example, the measuring chamber was designed for an angle of incidence of 67°, the first assumed value for an angle of incidence is selected to be used with the model may be a value above or below 67°, such as, for example, 69° or 65°. At step 414, a root mean square difference function is calculated which is an error value representing a comparison of the calculated values of $\Psi$ and $\Delta$ for the first assumption and the stored experimental values of $\Psi$ and $\Delta$. At step 416, the system checks to determine whether the minimum error has been found. That implies at least two error values must be compared; and therefore, on the first iteration, by definition, the minimum error cannot be found. At step 418, a second assumption for the angle of incidence is selected which is an assumed value intended to make the error value smaller, for example, a value converging toward the design value of 67°.

The process returns to step 412 where new $\Psi$ and $\Delta$ values are calculated; and at step 414, a root mean square difference compares the newly calculated $\Psi$ and $\Delta$ values to the stored experimental $\Psi$ and $\Delta$ values to produce a new root mean square difference value. At step 416, the new error value is compared to the previously calculated error values to determined whether a minimum error value has been found. The process in steps 412 through 418 iterates until the assumed angle of incidence producing the minimum error value is found. It should be noted that process of assuming angles of incidence may be accomplished by having assumed angles manually input, or an automatic routine may be used which provides the assumed angles of incidence in a logical manner until the minimum error value is found. The root mean square difference value is determined by the following $$\sqrt{(\psi_{exp} - \psi_{calc})^2 + (\Delta_{exp} - \Delta_{calc})^2}$$

Per step 420, it is preferred that the process of using a test sample to determine the angle of incidence as shown in steps 402 through 418 be repeated for second and third test thin film samples also having known refractive indices and film thicknesses. At step 422, the resulting three angles of incidence are then averaged to produce a final value of the calculated angle of incidence which is stored for use when analyzing production samples. The three test samples should preferably have different thicknesses of $SiO_2$ films on a Si substrate, for example, the film thicknesses may be 500 Å, 1000 Å, and 1500 Å thick.

When the device is operated on-line, the pallet 25 with a production sample 11 is moved into the vacuum chamber 9. Shutter 15 in front of the laser 14 is opened, and the X-Y scanner 12 is operated to scan the front surface 17 of the production sample as previously described. The scanner starts scanning at X-Y coordinates of a set position that located the front surface for the test sample which were stored during the scanning process for the test sample. Consequently, at the beginning of the scanning process, the reflected light beam 27 should be very close to the position aligning the reflected beam 27 from the front surface 17 of the production sample with the aperture 13 and photodetector 36. When the self aligning scanning beam capture algorithm is completed, the position of the light beam is further optimized for the largest signal magnitude and lowest contamination from scattered light by fine adjustment of the X-Y scanner 12 using the optimization routine. In the same manner as previously described, the rotating analyzer 28 is operated to collect sampled data points from which experimental values of the ellipsometric parameters are determined and stored. Using the same model as previously described with reference to the off-line measurement, the calculated angle of incidence is used with estimates of film thickness and index of refraction to calculate values of the ellipsometric parameters $\Psi$ and $\Delta$. A root mean square difference function is used to produce an error function resulting from a comparison of the experimental and calculated values of the ellipsometric parameters. New values for the film thickness and index of refraction are assumed until assumed values are found which provide a minimum error function.

The present invention, as illustrated in FIG. 1, is designed to have an angle of incidence of 67° for 1100 Å$S_3N_4$ film on a transparent polycarbonate sample. Production thin film samples are mounted on two sides of a rotatable pallet which is continuously loaded in and out of the test vacuum chamber every two minutes. The ellipsometer measures both the index of refraction and film thickness within 45 seconds. A theoretical calculation indicates that the angle of incidence is invariant within the mechanical tolerance of the sample position. The specifications for the mechanical tolerance of the system are ±0.5° for rotation of the sample position and ±1 mm for lateral displacement. Error analysis shows that for an 1100 Å $S_3N_4$ film on a transparent polycarbonate substrate with an angle of incidence of 67°, the error for measured film thickness would be ±5.4 Å and the error index of refraction would be ±0.001. Experimental results demonstrate that the measurements are accurate and repeatable.

The apparatus disclosed herein permits measurements of optical characteristics of the film even when the indices of refraction of the film and its substrate are very close. Further, if the sample is a stack of multilayer thin films, the apparatus of the invention may be used to practice Variable Angle Spectroscopic Ellipsometry in which the angle of incidence and a different wavelength for each film layer is used to measure the film layer thicknesses and other optical properties of the film layers. In another application, whether the substrate is opaque, such as aluminum or silicon, or transparent, such as polycarbonate or glass, or semitransparent, the invention may be used to find and analyze reflected beams off the front and rear surfaces of the sample to provide information about the film stack, the substrate or the film stack on the rear surface, as the case may be.

While embodiments of the present invention are described and illustrated in considerable detail, there is no intention to restrict, or in any way limit, the scope of the appended claims to such detail. Additional advantages and modifications will readily appear to those skilled in the art. For example, the invention may be practiced with other types of ellipsometers, such as, for example, a rotating polarizer ellipsometer. Also, while the pin hole is shown to be part of a pin hole plate, the pin hole may be integrated into other components such as the photodetector. Other error functions may be used to compare the measured and calculated values of the ellipsometric parameters. As will be appreciated, the invention is equally applicable to facilitate the measurement of other physical characteristics of thin film samples. The invention in its broadest aspects is therefore not limited to the specific details, representative apparatus and method, and illustrative examples shown and described. Accordingly, departures may be made from such details without departing from the spirit or scope of the general inventive concept.

What is claimed is:

1. A measuring station for use in a production line to measure a thin film characteristic of a thin film sample, the measuring station comprising:

a vacuum chamber having first and second windows;

a movable pallet for supporting the thin film sample and movable to a position in the vacuum chamber;

an ellipsometer having
   a source of collimated light and a polarizer for producing a polarized light beam, and
   a photodetector for producing an output signal in response to receiving a reflected light beam;

a scanner located with respect to said polarizer and said first window for receiving said polarized light beam and aiming an incident light beam through said first window and onto the thin film sample, said scanner moving said incident light beam to different locations on a surface of said thin film sample to direct the reflected light beam from the sample through said second window and onto said photodetector; and control means responsive to the output signal and connected to said scanner and said ellipsometer for providing control signals to cause said scanner to move the incident light beam to a location on a selected surface of the thin film sample producing a maximum intensity of the reflected light beam, operating said ellipsometer to determine ellipsometric parameters of the thin film sample, and determining the thin film characteristics of the thin film sample in response to the ellipsometric parameters and a stored angle of incidence determined with a different thin film sample.

2. The measuring station of claim 1 further comprising an aperture located relative to the photodetector and the selected surface of the thin film sample for limiting a quantity of the reflected light beam striking the photodetector.

3. A method for aligning an ellipsometer with a predetermined surface of a thin film sample, the ellipsometer having a source of collimated light and a photodetector, the photodetector producing an output signal as a function of an intensity of a reflected light beam from the thin film sample, the method comprising:

operating a scanner receiving the source of collimated light to direct an incident light beam to a set position relative to the predetermined surface of the thin film sample;

operating the scanner to move the incident light beam in a predetermined scanning pattern;

detecting a presence of the reflected light beam to locate the predetermined surface; and operating the scanner to move the incident light beam to a location on the predetermined surface of the thin film sample producing a maximum intensity of the reflected light beam from the predetermined surface of the thin film sample.

4. The method of claim 3 wherein the method further comprises the step of passing the reflected light beam through an aperture located between the thin film sample and the photodetector prior to the step of detecting the presence of the reflected light beam to locate the predetermined surface.

5. The method of claim 3 wherein the set position being chosen such that moving the incident light beam in the predetermined pattern will result in the reflected light beam from the predetermined surface being detected by the photodetector prior to a second reflected light beam from another surface of the thin film sample.

6. The method of claim 3 wherein the step of operating the scanner to move the incident light beam to a location on the predetermined surface of the thin film sample further comprises the steps of:

operating the scanner to move the incident light beam to different locations in a first direction;

sampling the output signal to measure the intensity of the reflected light beam with the photodetector at each of said different locations in said first direction;

stopping the operation of the scanner in response to the incident light beam being at a location in the first direction producing a maximum intensity of the reflected light beam from the predetermined surface of the thin film sample;

operating the scanner to move the incident light beam to different locations in a second direction;

sampling the output signal to measure the intensity of the reflected light beam with the photodetector at each of said different locations in said second direction; and stopping the operation of the scanner in response to the incident light beam being at a location in the second direction producing a maximum intensity of the reflected light beam from the predetermined surface of the thin film sample.

7. A method for aligning an ellipsometer with a selected surface of a thin film sample, the ellipsometer directing an incident light beam toward the thin film sample, and the ellipsometer including a photodetector producing an output signal as a function of an intensity of a reflected light beam from the thin film sample striking the photodetector, the method comprising the steps of:

a) moving the incident light beam with a scanner to a set position relative to the thin film sample as a function of the selected surface;

b) moving the incident light beam with the scanner a step in a first direction;

c) monitoring the photodetector to detect a presence of the output signal;

d) iterating steps and c)in response to not detecting the presence of the output signal;

e) moving the incident light beam with the scanner a step in a second direction substantially perpendicular to the first direction in response to moving the incident light beam a predetermined number of steps in the first direction without detecting the presence of the output signal;

f) moving the incident light beam with the scanner a step in a direction opposite the first direction;

g) monitoring the photodetector to detect the presence of the output signal;

h) iterating steps f) and g) in response to not detecting the presence of the output signal;

i) moving the incident light beam with the scanner a step in the second direction substantially perpendicular to the first direction in response to moving the incident light beam a predetermined number of steps in the direction opposite the first direction without detecting the presence of the output signal;

j) iterating steps b) through i) in response to not detecting the presence of the output signal;

k) stopping motion of the incident light beam with the scanner in response to detecting the presence of the output signal in steps c) and g); and l) stopping motion of the incident light beam with the scanner in response to moving the incident light beam a predetermined number of steps in the second direction without detecting the presence of the output signal.

8. The method of claim 7 wherein the method further comprises the steps of:

a) moving the incident light beam with the scanner a predetermined distance in a direction opposite the first direction;

b) moving the incident light beam a step in the first direction;

c) detecting a current magnitude of the output signal from the photodetector in response to moving the incident light beam the step in the first direction;

d) stopping motion of the incident light beam in the first direction in response to detecting a maximum magnitude of the output signal;

e) moving the incident light beam with the scanner a predetermined distance in a direction opposite the second direction;

f) moving the incident light beam a step in the second direction;

g) detecting a current magnitude of the output signal from the photodetector in response to moving the incident light beam the step in the second direction;

h) stopping motion of the incident light beam in the second direction in response to detecting a maximum magnitude of the output signal.

9. The method of claim 8 wherein the steps of stopping motion of the incident light in response to detecting a maximum intensity of the reflected light beam further comprise the steps of:

a) detecting whether the current magnitude is greater than or equal to a prior magnitude of the output signal;

b) stopping motion of the incident light beam in response to the detected current magnitude not being greater than or equal to the prior magnitude of the output signal from the photodetector.

10. The method of claim 9 wherein the step of stopping motion of the incident light beam in response to detecting a maximum intensity of the reflected light beam further comprises the step of moving the incident light a predetermined increment in an opposite direction from a direction being moved when the current magnitude is detected not to be greater than or equal to the prior magnitude.

11. The method of claim 7 wherein the method further comprises the step of passing the reflected light beam through an aperture located between the thin film sample and the photodetector.

12. A method for determining an angle of incidence of an incident light beam from an ellipsometer by analyzing a reflected light beam produced by a reflection of the incident light beam from surface of a thin film sample onto a photodetector, the method comprising the steps of:

positioning a first test thin film sample having a known film thickness and a known index of refraction with respect to the ellipsometer so that the incident light beam is directed on the test thin film sample;

operating the ellipsometer to determine experimental values of ellipsometric parameters based on reflected light from the first test thin film sample;

storing the experimental values of the ellipsometric parameters; and determining a first angle of incidence of the incident light beam on the first test thin film sample by a) selecting an assumed angle of incidence, b) determining calculated values of the ellipsometric parameters in response to the assumed angle of incidence, the known thin film thickness and the known index of refraction of the first test thin film sample, c) comparing the calculated values of the ellipsometric parameters for the assumed angle of incidence to the experimental values of the ellipsometric parameters to produce a difference value, d) iterating steps a), b) and c) for different values of the assumed angle of incidence to produce a plurality of difference values, e) detecting a minimum difference value, f) selecting an assumed angle of incidence associated with the minimum difference value as the first angle of incidence, and g) storing the first angle of incidence.

13. The method of claim 12 wherein the method further comprises the steps of:

a) positioning a second test thin film sample having a second known film thickness and a second known index of refraction with respect to the ellipsometer so that the incident light beam is directed on the second test thin film sample;

b) operating the ellipsometer to determine second experimental values of the ellipsometric parameters based on reflected light from the second test thin film sample;

c) storing the second experimental values of the ellipsometric parameters d) determining a second angle of incidence of the incident light beam on the second test thin film sample in response to the second experimental values of the ellipsometric parameters; and e) producing a final angle of incidence by taking an average of the first angle of incidence and the second angle of incidence.

14. The method of claim 13 wherein the method further comprises the step of iterating steps a) through d) for other test thin film samples.

15. A method for determining an angle of incidence of an incident light beam from an ellipsometer by analyzing a reflected light beam produced by a reflection of the incident light beam from a surface of a thin film sample onto a photodetector, the method comprising the steps of:

positioning a first test thin film sample having a known film thickness and a known index of refraction with respect to the ellipsometer so that the incident light beam is directed on the first test thin film sample;

operating the ellipsometer to determine experimental values of ellipsometric parameters based on reflected light from the first test thin film sample;

storing the experimental values of the ellipsometric parameters; and determining a first angle of incidence of the incident light beam on the first test thin film sample by a) selecting an assumed angle of incidence, b) determining calculated values of the ellipsometric parameters in response to the assumed angle of incidence, the known thin film thickness and the known index of refraction of the first test thin film sample, c) producing a difference value in accordance with the following $$\sqrt{(\psi_{exp} - \psi_{calc})^2 + (\Delta_{exp} - \Delta_{calc})^2}$$

where $\Psi_{exp}$ and $\Delta_{exp}$ are the experimental values of the ellipsometric parameters, and $\Psi_{calc}$ and $\Delta_{calc}$ are the calculated values of the ellipsometric parameters, d) iterating steps a), b) and c) for different values of the assumed angle of incidence to produce a plurality of difference values, e) detecting a minimum difference value, f) selecting an assumed angle of incidence associated with the minimum difference value as the first angle of incidence, and g) storing the first angle of incidence.

16. A method of determining an angle of incidence of an incident light beam from an ellipsometer by analyzing a reflected light beam produced by a reflection of the incident light beam from a surface of a thin film sample onto a photodetector, the thin film sample being located on a pallet being moved from station to station on a production line, the method comprising the steps of:

moving a first test thin film sample to a predetermined location in a vacuum chamber, the first test thin film sample having first known thin film characteristics;

operating a scanner receiving polarized light from the ellipsometer to aim the incident light beam through a window in the vacuum chamber onto a predetermined surface of the first test thin film sample and to move the incident light beam in a predetermined pattern to different locations on the predetermined surface of the first test thin film sample;

measuring the intensity of a reflected light beam at the different locations on the predetermined surface of the first test thin film sample;

stopping the operation of the scanner in response to moving the incident light beam to a location on the predetermined surface of the first test thin film sample producing a maximum intensity of the reflected light beam from the predetermined surface of the first test thin film sample;

operating the ellipsometer to determine ellipsometric parameters for the first test thin film sample; and determining a first angle of incidence of the incident light beam on the predetermined surface of the first test thin film sample using the ellipsometric parameters for the first test thin film sample and the first known thin film characteristics of the first test thin film sample.

17. The method of claim 16 wherein the method further comprises the steps of:

moving a second test thin film sample to the predetermined location in the vacuum chamber, the second test thin film sample having second known thin film characteristics;

operating the scanner to aim the incident light beam through the window in the vacuum chamber onto a predetermined surface of the second test thin film sample and to move the incident light beam in the predetermined pattern to different locations on the predetermined surface of the second test thin film sample;

measuring the intensity of the reflected light beam at the different locations on the predetermined surface of the second test thin film sample;

stopping the operation of the scanner in response to moving the incident light beam to a location on the predetermined surface of the second test thin film sample producing a maximum intensity of the reflected light beam from the predetermined surface of the second test thin film sample;

operating the ellipsometer to determine ellipsometric parameters for the second test thin film sample;

determining a second angle of incidence of the incident light beam on the predetermined surface of the second test thin film sample using the ellipsometric parameters for the second test thin film sample and the second known thin film characteristics of the second test thin film sample; and determining a final angle of incidence in response to the first and the second angles of incidence.

18. The method of claim 17 wherein the final angle of incidence is determined by averaging the first and the second angles of incidence.

19. The method of claim 18 wherein the method of determining an angle of incidence further comprises iterating the steps of claim 20 a predetermined number of times for a predetermined number of further test thin film samples and determining a final angle of incidence by averaging angles of incidence determined for each of the test thin film samples.

20. The method of claim 19 wherein the known thin film characteristics are index of refraction and film thickness of the test thin film samples.

21. A method Of measuring thin film characteristics of a thin film sample located on a pallet being moved from station to station on a production line comprising the steps of:

moving a test thin film sample having known thin film characteristics to a predetermined location in a vacuum chamber;

determining an angle of incidence of an incident light beam from an ellipsometer on a predetermined surface of the test thin film sample as a function of the known thin film characteristics of the test thin film sample;

storing the angle of incidence of the incident light beam on the predetermined surface of the test thin film sample;

moving a production thin film sample to the predetermined location in the vacuum chamber;

operating a scanner to move the incident light beam in a predetermined pattern to different locations on a predetermined surface of the first production thin film sample;

measuring the intensity of a reflected light beam at the different locations on the predetermined surface of the production thin film sample;

stopping the operation of the scanner in response to moving the incident light beam to a location on the predetermined surface of the production thin film sample producing a maximum intensity of the reflected light beam from the predetermined surface of the production thin film sample;

operating the ellipsometer to determine ellipsometric parameters for the production thin film sample; and determining the thin film characteristics of the production thin film sample using the ellipsometric parameters for the production thin film sample and the stored angle of incidence.

* * * * *

UNITED STATES PATENT AND TRADEMARK OFFICE
CERTIFICATE OF CORRECTION

PATENT NO. : 5,408,322
DATED : April 18, 1995
INVENTOR(S) : Hsu et al.

It is certified that error appears in the above-indentified patent and that said Letters Patent is hereby corrected as shown below:

Col. 7, line 30, delete "a" after "move". (first occurrence)

Col. 14, line 29, "steps and c)in" should be -- steps b) and c) in --.

Col. 15, line 41, insert "a" after "from".

Col. 15, line 47, insert "first" before "test".

Col. 18, line 18, "claim 20" should be -- claim 17 --.

Signed and Sealed this

Seventh Day of November, 1995

Attest:

BRUCE LEHMAN

Attesting Officer    Commissioner of Patents and Trademarks